(12) United States Patent
Haluszczuk et al.

(10) Patent No.: US 12,215,081 B2
(45) Date of Patent: Feb. 4, 2025

(54) PHARMACEUTICAL INTERMEDIATE

(71) Applicant: ZAKLADY FARMACEUTYCZNE POLPHARMA S.A., Starogard Gdanski (PL)

(72) Inventors: Adam Haluszczuk, Gdansk (PL); Dorota Pogoda, Syrynia (PL)

(73) Assignee: ZAKLADY FARMACEUTYCZNE POLPHARMA S.A., Starogard Gdanski (PL)

( * ) Notice: Subject to any disclaimer, the term of this patent is extended or adjusted under 35 U.S.C. 154(b) by 725 days.

(21) Appl. No.: 17/609,034

(22) PCT Filed: May 20, 2020

(86) PCT No.: PCT/EP2020/064126
§ 371 (c)(1),
(2) Date: Nov. 5, 2021

(87) PCT Pub. No.: WO2020/234383
PCT Pub. Date: Nov. 26, 2020

(65) Prior Publication Data
US 2022/0213037 A1  Jul. 7, 2022

(30) Foreign Application Priority Data
May 22, 2019 (EP) .................... 19460027

(51) Int. Cl.
C07D 211/58 (2006.01)
(52) U.S. Cl.
CPC ................. C07D 211/58 (2013.01)
(58) Field of Classification Search
None
See application file for complete search history.

(56) References Cited

U.S. PATENT DOCUMENTS 10,343,993 B2  7/2019 Biljan et al.
10,807,953 B2  10/2020 Biljan et al.
(Continued)

FOREIGN PATENT DOCUMENTS

CN       108358817 A        8/2018
WO   WO-2006036874 A1  *  4/2006  ........... C07D 211/58
(Continued)

OTHER PUBLICATIONS

International Search Report dated Jun. 26, 2020 issued in corresponding PCT/EP2020/064126 application (3 pages).

*Primary Examiner* — Jeffrey S Lundgren
*Assistant Examiner* — Anthony Joseph Seitz
(74) *Attorney, Agent, or Firm* — Millen White Zelano & Branigan; Csaba Henter

(57) ABSTRACT

This invention relates to 4-(4-fluorobenzylamino)-1-methylpiperidine trihydrate and a process for the preparation of 4-(4-fluorobenzylamino)-1-methylpiperidine trihydrate comprising treating 4-(4-fluorobenzylamino)-1-methylpiperidine with water.

The invention also relates to a process for the preparation of pimavanserin comprising reacting 4-(4-fluorobenzylamino)-1-methylpiperidine trihydrate with 1-isobutoxy-4-(isocyanatomethyl)benzene; to a process for the preparation of a pimavanserin acid addition salt comprising reacting 4-(4-fluorobenzylamino)-1-methylpiperidine trihydrate with 1-isobutoxy-4-(isocyanatomethyl)benzene and converting pimavanserin into a pimavanserin acid addition salt, pimavanserin and pimavanserin acid addition salts obtainable by the process, and to the use of 4-(4-fluorobenzylamino)-1-methylpiperidine trihydrate for preparing pimavanserin or an acid addition salt thereof.

8 Claims, 1 Drawing Sheet

(56) References Cited

U.S. PATENT DOCUMENTS

| | | |
|---|---|---|
| 2018/0037549 A1 | 2/2018 | Biljan et al. |
| 2019/0276401 A1 | 9/2019 | Biljan et al. |

FOREIGN PATENT DOCUMENTS

| | | | | |
|---|---|---|---|---|
| WO | WO-2008144326 A2 | * | 11/2008 | ......... A61K 31/4468 |
| WO | WO-2009039461 A2 | * | 3/2009 | ........... C07D 211/58 |
| WO | 2016/141003 A1 | | 9/2016 | |
| WO | WO-2019040107 A1 | * | 2/2019 | ......... A61K 31/4468 |

* cited by examiner

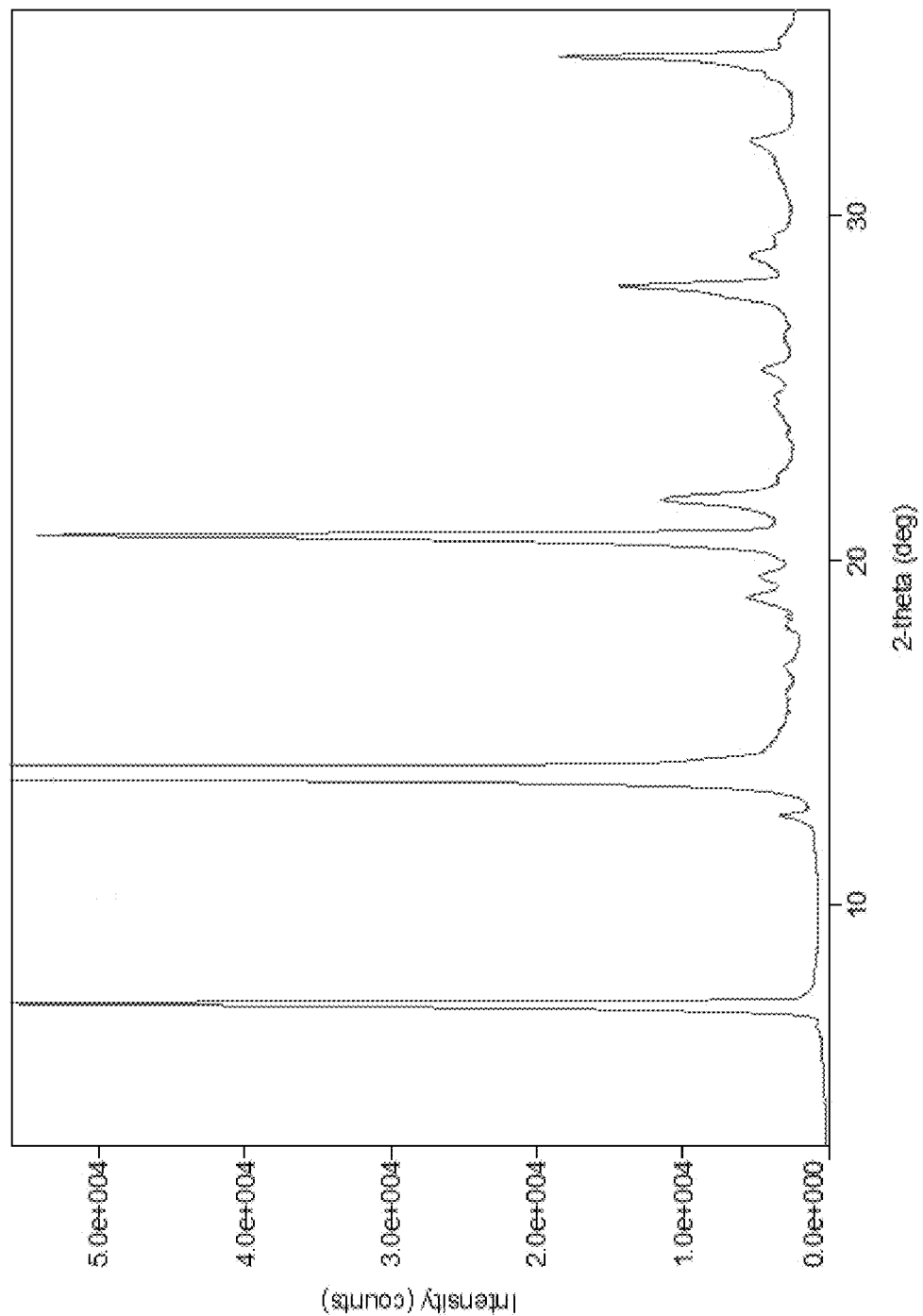

PHARMACEUTICAL INTERMEDIATE

The present invention relates to a pharmaceutical intermediate, particularly 4-(4-fluorobenzylamino)-1-methylpiperidine trihydrate, and a process for preparing 4-(4-fluorobenzylamino)-1-methylpiperidine trihydrate. The present invention also relates to the preparation of pimavanserin or an acid addition salt thereof using 4-(4-fluorobenzylamino)-1-methylpiperidine trihydrate.

Pimavanserin is named 1-[(4-fluorophenyl)methyl]-1-(1-methylpiperidin-4-yl)-3-{[4-(2-methylpropoxy)phenyl]methyl}urea and has the following structure:

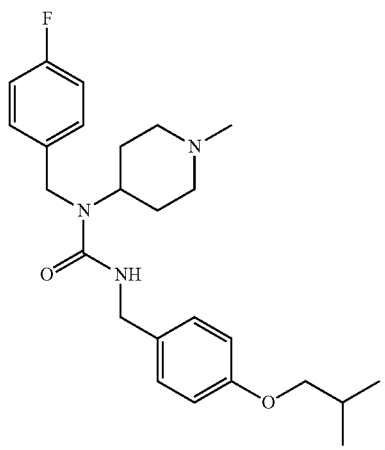 [SMILES: CC(C)COc1ccc(CNC(=O)N(Cc2ccc(F)cc2)C2CCN(C)CC2)cc1]

Pimavanserin is an atypical antipsychotic agent which acts as an inverse agonist and antagonist of the serotonin 5-HT$_{2A}$ receptor.

Pimavanserin is marketed in the USA as Nuplazid®. Nuplazid® contains pimavanserin hemitartrate, and is indicated for the treatment of hallucinations and delusions associated with Parkinson's disease psychosis (also known as PDP). Nuplazid® is prescribed as an oral dosage form.

Pimavanserin hemitartrate, 1-(4-fluorobenzyl)-3-(4-isobutoxybenzyl)-1-(1-methylpiperidin-4-yl)urea L-hemitartrate, has the following structure:

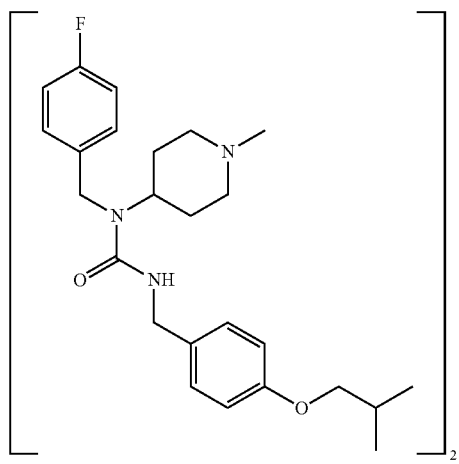

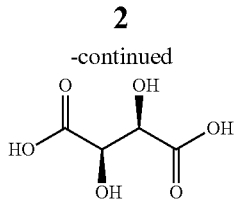

WO 2008/144326 and WO 2016/141003 relate to processes for preparing pimavanserin and pimavanserin hemitartrate, wherein the key synthetic step involves a condensation reaction between 4-(4-fluorobenzylamino)-1-methylpiperidine and 1-isobutoxy-4-(isocyanatomethyl)benzene to form pimavanserin:

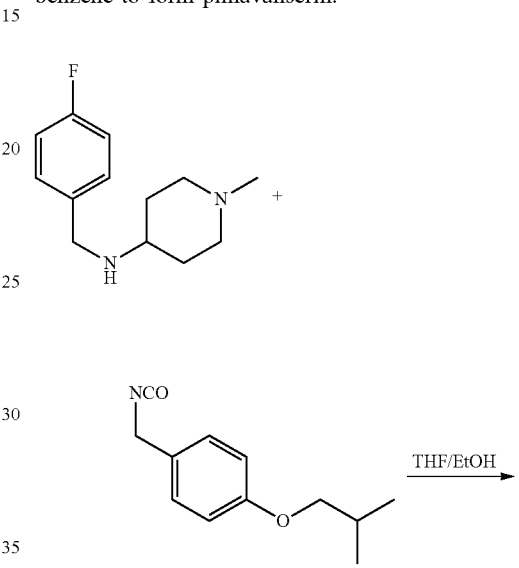

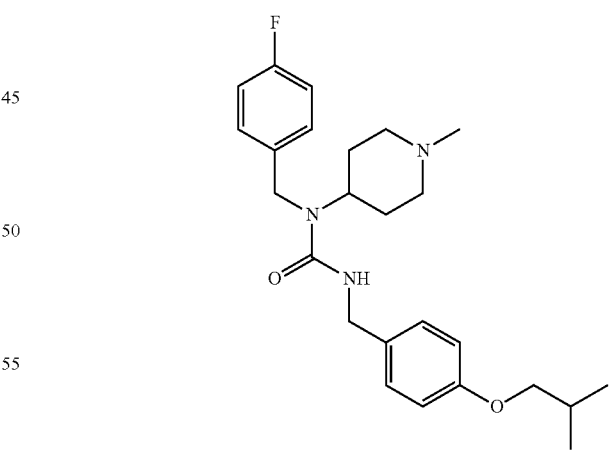

WO 2008/144326 and WO 2016/141003 also disclose processes to prepare the reagents used in the condensation reaction. In particular, preparations of 4-(4-fluorobenzylamino)-1-methylpiperidine are described which involve reductive amination reactions between 1-methyl-4-piperidone and 4-fluorobenzylamine, and 4-fluorobenzaldehyde and 1-methylpiperidin-4-amine.

WO 2008/144326

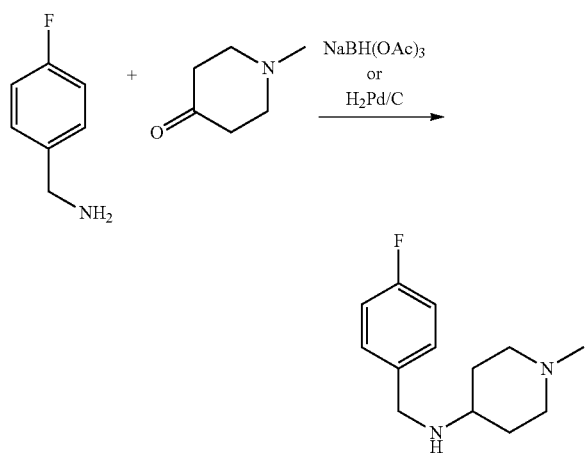

WO 2016/141003

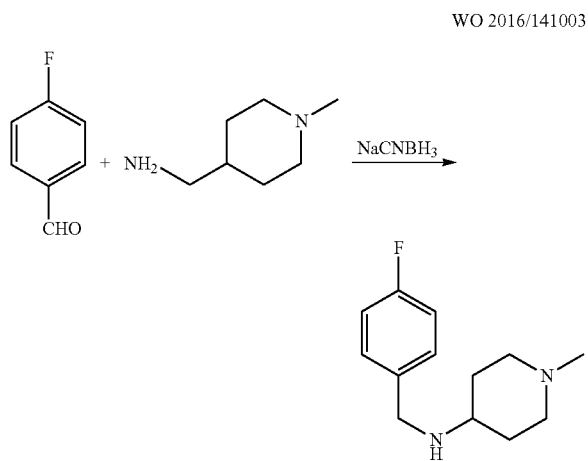

As shown by the reaction scheme depicted above, 4-(4-fluorobenzylamino)-1-methylpiperidine is a key reagent used in the preparation of pimavanserin. 4-(4-fluorobenzylamino)-1-methylpiperidine is also known in the art as N-([(4-fluorophenyl)methyl]-1-methy-4-piperidineamine) and N-((4-fluorobenzyl)-1-methylpiperidin-4-amine).

Unfortunately, the processes described in WO 2008/144326 and WO 2016/141003 provide 4-(4-fluorobenzylamino)-1-methylpiperidine with sub-optimal purity, and although 4-(4-fluorobenzylamino)-1-methylpiperidine can also be purchased directly from commercial suppliers, the same problem persists.

Sub-optimal purity of 4-(4-fluorobenzylamino)-1-methylpiperidine is known to be caused by unreacted starting materials (I) and (II), and under- and over-reduced addition products (III) and (IV):

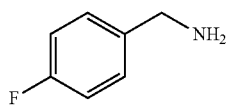

I

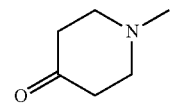

II

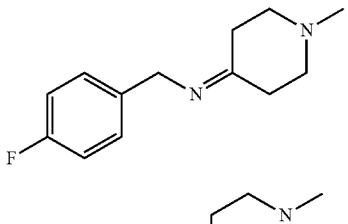

III

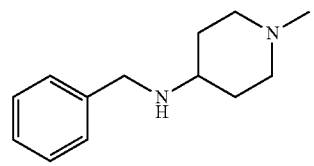

IV

Unsurprisingly, these impurities have similar electrostatic and solubility characteristics to 4-(4-fluorobenzylamino)-1-methylpiperidine which makes them difficult to remove using simple purification or washing procedures. Moreover, because 4-(4-fluorobenzylamino)-1-methylpiperidine is an oily liquid recrystallisation processes that are commonly used to purify chemical intermediates and products cannot be used.

Therefore, 4-(4-fluorobenzylamino)-1-methylpiperidine is typically used as synthesised (or as purchased) directly in the pimavanserin-forming reaction step.

To prevent the requirement for direct use of 4-(4-fluorobenzylamino)-1-methylpiperidine, WO 2016/141003 discloses conversion of 4-(4-fluorobenzylamino)-1-methylpiperidine into crystalline 4-(4-fluorobenzylamino)-1-methylpiperidine di hydrochloride. However, 4-(4-fluorobenzylamino)-1-methylpiperidine dihydrochloride must be converted to its corresponding free base before being used in the final pimavanserin-forming reaction step. Therefore the use of the dihydrochloride salt necessitates an additional step in the preparation of pimavanserin.

Indeed, both large-scale chemical syntheses and purifications are subjected to constant review and optimisation. Owing to economies of scale, any small improvement in a given reaction or purification parameter is particularly economically significant. Therefore, optimisation of a large-scale synthesis or purification that provides, for example, an increase in chemical yield, decrease in step-to-step manipulation, decrease in reaction time, decrease in reaction temperature, decrease in amount of catalyst or solvent used, increase in the favourability of reagents, reduction in side-product formation, a more environmentally benign synthesis or increase in chemical purity is of interest both to chemical manufacturers and suppliers.

Moreover, step optimisation that reduces the need for multiple or hard-to-perform purifications are particularly beneficial. Any improvement in the ease of purification or isolation, through telescoping (wherein two or more, previously independent synthetic transformations converge into a "single" process and therefore require only one purification step) of synthetic procedures, or the identification of an intermediate for recrystallisation, or precipitation, or removal of impurities through conversion into a transient intermediate, or substitution for a cheaper, more environmentally friendly or less toxic reagent, provide an attractive and economically desirable goal. In situations where more traditional purification procedures yield poor or unsuitable results, it becomes necessary that more innovative solutions are required.

However, practical achievement of any such improvement is not straightforward, and even careful optimisation of individual parameters of a synthetic or purification step will often fail to provide a workable advantage within an overall production process.

Consequently, because 4-(4-fluorobenzylamino)-1-methylpiperidine is a key reagent in the final bond-forming step to provide pimavanserin, it would be highly desirable to provide 4-(4-fluorobenzylamino)-1-methylpiperidine with increased purity and yield. This would reduce or prevent the presence of impurities (I)-(IV) in the final pimavanserin product, as well as any other impurities generated from side-reactions between compounds (I)-(IV) with 1-isobutoxy-4-(isocyanatomethyl)benzene in the pimavanserin-forming reaction step. Consequently, further optimisation of the purity of 4-(4-fluorobenzylamino)-1-methylpiperidine is desirable.

Accordingly, the present invention provides 4-(4-fluorobenzylamino)-1-methylpiperidine trihydrate.

4-(4-Fluorobenzylamino)-1-methylpiperidine trihydrate has the following structure:

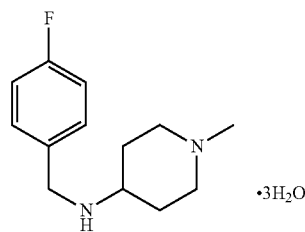 [SMILES: CN1CCC(NCc2ccc(F)cc2)CC1]

Advantageously, it has been found that 4-(4-fluorobenzylamino)-1-methylpiperidine trihydrate is solid. Preferably, 4-(4-fluorobenzylamino)-1-methylpiperidine trihydrate is crystalline.

It has also been found that 4-(4-fluorobenzylamino)-1-methylpiperidine trihydrate demonstrates improved stability and purity in comparison to the 4-(4-fluorobenzylamino)-1-methylpiperidine oil disclosed in the prior art.

Advantageously, 4-(4-fluorobenzylamino)-1-methylpiperidine trihydrate can be used directly in the pimavanserin-forming reaction step to prepare pimavanserin, whereas 4-(4-fluorobenzylamino)-1-methylpiperidine dihydrochloride as mentioned hereinabove cannot.

The present invention will now be described with reference to the accompanying drawing, in which:

FIG. 1 shows the XRPD diffractogram for 4-(4-fluorobenzylamino)-1-methylpiperidine trihydrate.

4-(4-Fluorobenzylamino)-1-methylpiperidine trihydrate crystallises in a monoclinic system space group $P2_1/n$, with two molecules of 4-(4-fluorobenzylamino)-1-methylpiperidine and six water molecules in the asymmetric unit.

4-(4-Fluorobenzylamino)-1-methylpiperidine trihydrate has a melting point of approximately 37-42° C. as measured by differential scanning calorimetry (DSC) performed at a heating rate of 10° C./min, and a characteristic X-ray powder diffractogram and IR spectrum;

The characterising peaks are reported as follows:
XRPD 2θ (°)±0.2°: 7.1, 12.6, 13.9, 18.8, 19.5, 20.7, 21.8, 27.7, 32.2 and 34.6.

IR ($cm^{-1}$): 576, 771, 825, 898, 1072, 1103, 1156, 1218, 1277, 1378, 1436, 1451, 1468, 1508, 1601, 1647, 2685, 2740, 2798, 2851, 2941 and 3411.

Details for the analytical methods can be found in the "Analytical methods" section.

Accordingly, the present invention also provides a process for the preparation of 4-(4-fluorobenzylamino)-1-methylpiperidine trihydrate, preferably as crystalline solid, comprising treating 4-(4-fluorobenzylamino)-1-methylpiperidine with water.

It has been found that 4-(4-fluorobenzylamino)-1-methylpiperidine oil can be converted in a single step to 4-(4-fluorobenzylamino)-1-methylpiperidine trihydrate, a pure white crystalline solid.

Advantageously, the conversion of commercially sourced 4-(4-fluorobenzylamino)-1-methylpiperidine oil of sub-optimal purity into 4-(4-fluorobenzylamino)-1-methylpiperidine trihydrate can be achieved in near quantitative yield (90-100%) and with no detectable impurities.

In view of the prior art, the process removes the requirement for purifying 4-(4-fluorobenzylamino)-1-methylpiperidine by high-vacuum and/or high-temperature distillation. The process also offers advantages in view of 4-(4-fluorobenzylamino)-1-methylpiperidine dihydrochloride, because 4-(4-fluorobenzylamino)-1-methylpiperidine trihydrate does not have to be treated with a base (i.e. to generate the free amine) before taking part in a further reaction i.e. to prepare pimavanserin. Moreover, the use of water to prepare a solid intermediate versus the use of hydrochloric acid is also economically and environmentally advantageous.

More generally, the process is also economically and environmentally advantageous because water is a cheap environmentally friendly solvent, and the process proceeds quickly which limits reactor time and thus energy needed.

Moreover, crystalline 4-(4-fluorobenzylamino)-1-methylpiperidine trihydrate demonstrates improved chemical stability compared to 4-(4-fluorobenzylamino)-1-methylpiperidine oil, and since it is a crystalline solid it is also easier to handle on both small- and large-scale.

4-(4-Fluorobenzylamino)-1-methylpiperidine may be prepared as follows:

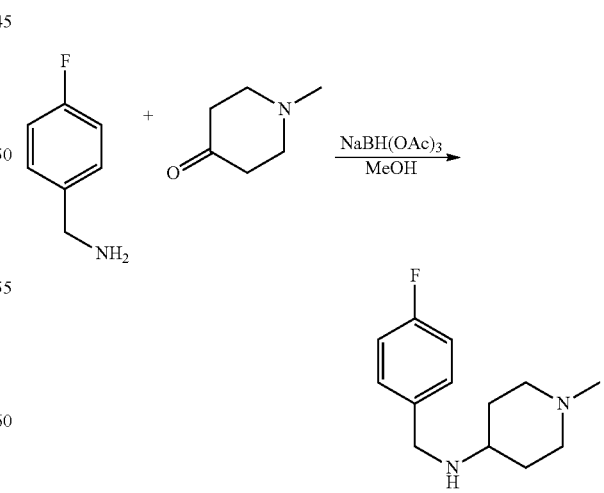

The structure and preparation of 4-(4-fluorobenzylamino)-1-methylpiperidine trihydrate according to the present invention are as follows:

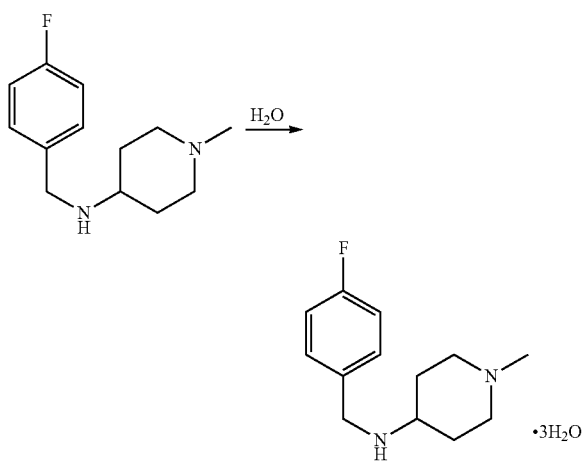

In one embodiment, 4-(4-fluorobenzylamino)-1-methylpiperidine trihydrate is prepared by treating 4-(4-fluorobenzylamino)-1-methylpiperidine with water.

Preferably, 4-(4-fluorobenzylamino)-1-methylpiperidine is dissolved in water at ambient temperature, i.e. room temperature or 20-25° C. and 4-(4-fluorobenzylamino)-1-methylpiperidine trihydrate is formed.

The 4-(4-fluorobenzylamino)-1-methylpiperidine trihydrate may also be prepared by treating 4-(4-fluorobenzylamino)-1-methylpiperidine with a mixture of water and an alcohol. For example, 4-(4-fluorobenzylamino)-1-methylpiperidine trihydrate may be prepared by treating 4-(4-fluorobenzylamino)-1-methylpiperidine with a mixture of water and an alcohol selected from methanol, ethanol, propanol and butanol. In such cases the water/alcohol mixture may comprise a 90/10 (v/v) mixture of water and alcohol, for example a 90/10 (v/v) mixture of water and methanol.

The 4-(4-fluorobenzylamino)-1-methylpiperidine trihydrate may also be prepared by treating 4-(4-fluorobenzylamino)-1-methylpiperidine with a mixture of water and an organic solvent. For example, 4-(4-fluorobenzylamino)-1-methylpiperidine trihydrate may be prepared by treating 4-(4-fluorobenzylamino)-1-methylpiperidine with a mixture of water and an organic solvent selected from acetone, acetonitrile, dimethyl ether, 1,4-dioxane and THF. In such cases the water/organic solvent mixture may comprise a 90/10 (v/v) mixture of water and organic solvent, for example a 90/10 (v/v) mixture of water and THF.

The 4-(4-fluorobenzylamino)-1-methylpiperidine trihydrate may also be prepared by treating 4-(4-fluorobenzylamino)-1-methylpiperidine with an aqueous inorganic salt solution. In such cases the water may contain 10% (weight percent) of an inorganic salt, for example a 10% KCl solution in water.

The use of a water/alcohol mixture, a water/organic solvent mixture is also advantageous for preparing 4-(4-fluorobenzylamino)-1-methylpiperidine trihydrate, as the addition of the non-water solvent increases the solubility of the 4-(4-fluorobenzylamino)-1-methylpiperidine. On the other hand, the use of an aqueous inorganic salt solution is also advantageous for preparing 4-(4-fluorobenzylamino)-1-methylpiperidine trihydrate, as the addition of the inorganic salt to water increases the rate at which the 4-(4-fluorobenzylamino)-1-methylpiperidine crystallizes.

In one embodiment, the process for the preparation of 4-(4-fluorobenzylamino)-1-methylpiperidine trihydrate comprises treating 4-(4-fluorobenzylamino)-1-methylpiperidine with water, preferably by:
(i) dissolving 4-(4-fluorobenzylamino)-1-methylpiperidine in water to form a solution;
(ii) cooling the solution obtained in step (i) to precipitate 4-(4-fluorobenzylamino)-1-methylpiperidine trihydrate; and
(iii) isolating the 4-(4-fluorobenzylamino)-1-methylpiperidine trihydrate from the solution.

In step (i) the 4-(4-fluorobenzylamino)-1-methylpiperidine may also be dissolved in a water/alcohol mixture, a water/organic solvent mixture or an aqueous inorganic salt solution as described hereinabove.

Cooling the solution in step (ii) increases the rate of recrystallisation of the 4-(4-fluorobenzylamino)-1-methylpiperidine trihydrate compared to the recrystallisation rate at room temperature, and thus advantageously reduces the amount of time required to prepare the intermediate.

Preferably in step (ii), the solution is cooled to a temperature below 20° C. In practice, any temperature below 20° C. is suitable for inducing crystallisation of 4-(4-fluorobenzylamino)-1-methylpiperidine trihydrate, providing temperatures at which ice crystals of water form i.e. 0° C. are avoided.

The solution may be cooled to below 20° C., preferably to 15° C. and 1° C., most preferably to 15° C.

After the solution is cooled it may then be stirred and the cooling temperature maintained. Preferably in step (ii), the cooled solution is stirred for 1-180 minutes before 4-(4-fluorobenzylamino)-1-methylpiperidine trihydrate is isolated from the solution. Stirring of the solution in conjunction with the maintenance of the cooling temperature ensures maximum conversion and crystallisation of 4-(4-fluorobenzylamino)-1-methylpiperidine to 4-(4-fluorobenzylamino)-1-methylpiperidine trihydrate.

The duration of the stirring may be extended depending upon the scale of the reaction i.e. the amount of 4-(4-fluorobenzylamino)-1-methylpiperidine trihydrate being prepared.

In one embodiment, prior to treating 4-(4-fluorobenzylamino)-1-methylpiperidine with water, the process comprises the step of preparing 4-(4-fluorobenzylamino)-1-methylpiperidine by reacting together 1-methyl-4-piperidone and 4-fluorobenzylamine or 4-fluorobenzaldehyde and 1-methylpiperidin-4-amine, in the presence of a reducing agent.

Preferably the reducing agent is selected from one which is suitable for reducing an imine functional group to the corresponding amine functional group. Suitable reducing agents are sodium cyanoborohydride ($NaBH_3CN$), sodium borohydride ($NaBH_4$), sodium tri-acetoxyborohydride ($NaBH(OAc)_3$) or hydrogen gas used in combination with a Pd/C catalyst.

Accordingly, the present invention also provides a process for the preparation of pimavanserin comprising reacting 4-(4-fluorobenzylamino)-1-methylpiperidine trihydrate with 1-isobutoxy-4-(isocyanatomethyl)benzene to form pimavanserin.

In one embodiment, the present invention also provides a process for the preparation of a pimavanserin acid addition salt comprising reacting 4-(4-fluorobenzylamino)-1-methylpiperidine trihydrate with 1-isobutoxy-4-(isocyanatomethyl)benzene to form pimavanserin, and converting pimavanserin into a pimavanserin acid addition salt.

Advantageously, 4-(4-fluorobenzylamino)-1-methylpiperidine trihydrate provides a hydrated form of 4-(4-fluorobenzylamino)-1-methylpiperidine with increased purity and chemical stability compared to forms disclosed in the prior art. Consequently, using 4-(4-fluorobenzylamino)-1-methylpiperidine trihydrate in the final step of preparing pimavanserin or a salt thereof also provides the corresponding active ingredient with increased level of purity.

The pimavanserin is preferably converted into a pharmaceutically acceptable acid addition salt. The term "pharmaceutically acceptable acid addition salt" refers to an acid addition salt of a compound that does not cause significant irritation to an organism to which it is administered. Preferred pharmaceutically acceptable salts can be selected from hydrochloride, hydrobromide, sulfate, phosphate, aliphatic or aromatic carboxylic or sulfonic acids, for example tartaric, acetic, succinic, lactic, malic, citric, ascorbic, nicotinic, methanesulfonic, ethanesulfonic, p-toluensulfonic, salicylic or naphthalenesulfonic acid.

The skilled person is well-equipped to determine the necessary conditions required to perform a salt formation reaction, and any such method contained within his common general knowledge is envisaged as being suitable.

Preferably, the process provides for the preparation of pimavanserin hemitartrate comprising reacting 4-(4-fluorobenzylamino)-1-methylpiperidine trihydrate with 1-isobutoxy-4-(isocyanatomethyl)benzene and converting pimavanserin into pimavanserin hemitartrate.

Typically, pimavanserin is converted to pimavanserin hemitartrate by treating a solution of pimavanserin with a solution of tartaric acid. For example, a solution of pimavanserin in ethanol is treated with a solution of tartaric acid in ethanol.

The pimavanserin may be converted to pimavanserin hemitartrate by treating a solution of pimavanserin in a solvent mixture, wherein the first solvent is selected from acetone and methyl-ethyl-ketone; and the second solvent is selected from methyl-t-butyl ether, THF, Me-THF and heptane, with a solution of tartaric acid in acetone. Preferably, pimavanserin is dissolved in a mixture of methyl-t-butyl ether and acetone and treated with a solution of tartaric acid in acetone.

Pimavanserin may be dissolved in a solvent mixture, wherein the first solvent is selected from acetone and methyl-ethyl-ketone; and the second solvent is selected from methyl-t-butyl ether, THF, Me-THF and heptane. Preferably, pimavanserin is dissolved in a mixture of methyl-t-butyl ether and acetone. Following dissolution, a seed of pimavanserin hemitartrate form C may be added to the solution containing pimavanserin, and the resulting mixture is heated to reflux. Preferably where pimavanserin and a seed of pimavanserin hemitartrate form C are dissolved in a mixture of methyl-t-butyl ether and acetone, the mixture is heated to reflux at 50-55° C. Following addition of the seed of pimavanserin hemitartrate form C, a solution of tartaric acid, preferably a solution of tartaric acid in acetone, is added to the solution containing pimavanserin and the seed of pimavanserin hemitartrate form C, and heating at reflux temperature is maintained.

Preferably, pimavanserin and tartaric acid are then allowed to react together in the presence of the seed of pimavanserin hemitartrate form C. Preferably, the reaction is conducted at reflux for at least 1 hour, and the pimavanserin hemitartrate obtained is pimavanserin hemitartrate form C.

Advantageously, this step converts pimavanserin to pimavanserin hemitartrate form C. Without wishing to be bound by theory, it is thought that the addition of the seed of pimavanserin hemitartrate form C prior to treating pimavanserin with a solution of tartaric acid assists the formation of pimavanserin hemitartrate form C as the final product.

Pimavanserin and tartaric acid may be allowed to react together in the absence of a seed of pimavanserin hemitartrate form C. Preferably, the reaction is conducted at reflux for at least 1 hour, and the pimavanserin hemitartrate obtained is pimavanserin hemitartrate.

WO 2008/144326 describes obtaining pimavanserin hemitartrate in various other crystalline forms (forms A-F) by reference to characteristic X-ray powder diffractograms, the characterising peaks of which are reported therein.

Form C is the preferred polymorphic form of pimavanserin hemitartrate owing to its increased chemical and physical stability over other known forms.

As reported by WO 2008/144326, the X-ray powder diffractogram of pimavanserin hemitartrate form C has characteristic peaks as follows.

XRPD $2\theta$ (°): 7.3, 8.2, 11.9, 12.8, 13.5, 14.3, 15.1, 16.0, 16.8, 17.2, 18.3, 18.9, 19.4, 20.3, 21.7, 22.5, 23.6, 24.0, 25.5, 25.7, 26.1, 27.5, 29.0 and 30.5.

Seed material of pimavanserin hemitartrate form C can be prepared as described in WO 2008/144326.

Accordingly, the present invention also includes process for preparing a dosage form comprising pimavanserin or an acid addition salt thereof, comprising the steps of preparing pimavanserin or an acid addition salt thereof according to the invention and combining the pimavanserin or the acid addition salt thereof with one or more pharmaceutically acceptable excipients.

Preferably, the present invention also includes a process for preparing a dosage form comprising pimavanserin hemitartrate, comprising the steps of preparing pimavanserin hemitartrate according to the invention and combining the pimavanserin hemitartrate with one or more pharmaceutically acceptable excipients.

Pimavanserin is typically administered orally and so the dosage form is preferably an oral dosage form, most preferably a tablet. In such a case, the process further comprises a tableting step.

The oral dosage form may be a coated or uncoated tablet and may be prepared using standard techniques known in the art.

Where the oral dosage form is a coated tablet, the tablet is preferably a film-coated tablet. Typically, the film-coated tablet will contain 20 mg of pimavanserin hemitartrate, which is equivalent to 17 mg of pimavanserin free base. Excipients formulated with the active ingredient typically include pregelatinised starch, magnesium stearate, and microcrystalline cellulose. Additionally, the film-coat is typically formulated with excipients which include hypromellose, talc, titanium dioxide, polyethylene glycol, and saccharin sodium.

Accordingly, the invention also provides pimavanserin obtainable by the process of the invention.

That is, pimavanserin obtainable by the process of reacting 4-(4-fluorobenzylamino)-1-methylpiperidine trihydrate with 1-isobutoxy-4-(isocyanatomethyl)benzene to form pimavanserin.

Accordingly, the invention also provides a pimavanserin acid addition salt obtainable by the process of the invention.

That is, a pimavanserin acid addition salt obtainable by the process of reacting 4-(4-fluorobenzylamino)-1-methylpiperidine trihydrate with 1-isobutoxy-4-(isocyanatomethyl)benzene to form pimavanserin, and converting pimavanserin into a pimavanserin acid addition salt.

Preferably, the pimavanserin acid addition salt is pimavanserin hemitartrate.

Accordingly, the invention also provides a pimavanserin or a pimavanserin acid addition salt dosage form obtainable by the process of the invention.

The products obtainable by the processes of the invention are different to the products obtainable by the processes of the prior art. As mentioned hereinabove, 4-(4-fluorobenzylamino)-1-methylpiperidine trihydrate provides a hydrated form of 4-(4-fluorobenzylamino)-1-methylpiperidine with increased purity and chemical stability compared to forms disclosed in the prior art. Consequently, using 4-(4-fluorobenzylamino)-1-methylpiperidine trihydrate in the final step of preparing pimavanserin or an acid addition salt thereof also provides this active ingredient with increased level of purity.

Accordingly, the invention also relates to the use of 4-(4-fluorobenzylamino)-1-methylpiperidine trihydrate for preparing pimavanserin or an acid addition salt thereof.

In a preferred embodiment, the invention relates to the use of 4-(4-fluorobenzylamino)-1-methylpiperidine trihydrate for preparing pimavanserin hemitartate.

Advantageously, using 4-(4-fluorobenzylamino)-1-methylpiperidine trihydrate to prepare pimavanserin or an acid addition salt thereof provides pimavanserin or an acid addition salt thereof with high levels of purity. Advantageously, the characteristic high purity of 4-(4-fluorobenzylamino)-1-methylpiperidine trihydrate is transferred from the trihydrate to pimavanserin or an acid addition salt thereof, when 4-(4-fluorobenzylamino)-1-methylpiperidine trihydrate is used in a process to prepare pimavanserin or an acid addition salt thereof.

In all embodiments of the invention preferably purified i.e. distilled water is used for the step of converting 4-(4-fluorobenzylamino)-1-methylpiperidine into 4-(4-fluorobenzylamino)-1-methylpiperidine trihydrate, however the use of tap water also provides acceptable levels of increased purity.

Advantageously, 4-(4-fluorobenzylamino)-1-methylpiperidine trihydrate

The present invention will now be described with reference to the following examples, which are not intended to be limiting.

Analytical Methods

IR:
IR spectra were recorded using a Perkin Elmer Spectrum Two spectrometer. IR spectra were recorded in KBr.

Gas Chromatography
Gas chromatograph with flame-ionization detector FID was used.
Column capillary; dimensions: 60 m×0.32 mm ID×1.5 µm; stationary phase (14%)-cyanopropylphenyl-(86%)-dimethyl polysiloxane; carrier gas-helium HPLC
A liquid chromatograph with UV detector adjusted to ultra performance liquid chromatography was used.
Column Acquity UPLC CSH C18; mobile phase A—0.1% methanesulfonic acid in water, mobile phase B—acetonitrile; column temperature 25° C.; flow rate 0.30 mL/min.

DSC
Differential scanning calorimetry (DSC) measurements were performed using a DSC1 Start System Mettler Toledo Instrument. Samples were tested in 40 µl aluminum crucibles (3-6 mg), preliminary hermetically pressed and next punctured, under nitrogen flow (40 ml/min), within the temperature range from 0.0° C. to 300.0° C. in a dynamic segment at heating rate of 10.0° C./min.

XRPD
Diffraction peaks intensity data were collected on an IPDS 2T dual-beam diffractometer (STOE & Cie GmbH, Darmstadt, Germany) at 120.0(2) K with MoKα radiation of a microfocus X-ray source (GeniX 3D Mo High Flux, Xenocs, Sassenage, 50 kV, 1.0 mA, λ=0.71069 Å). The investigated crystal was thermostated in nitrogen stream at 120 K during the entire experiment.

EXAMPLES

Example 1: Preparation of 4-(4-fluorobenzylamino)-1-methylpiperidine

Sodium triacetoxyborohydride was added portionwise to a mixture of N-methylpiperid-4-one and 4-fluorobenzylamine in methanol, and the mixture was allowed to stir for 24 hours. The reaction progress was monitored by TLC (4-fluorobenzylamine). When the reaction was complete a solution of NaOH was added to the mixture, and the methanol was distilled out under vacuum (below 45° C.). The remaining mixture was cooled to room temperature (20-25° C.) and extracted with methyl-t-butyl ether. The methyl-t-butyl ether extracts were then combined and washed with sodium sulfate, and the methyl-t-butyl ether was then distilled out at atmospheric pressure, and then under vacuum to obtain crude 4-(4-fluorobenzylamino)-1-methylpiperidine as an oil.

Example 2: Preparation of 4-(4-fluorobenzylamino)-1-methylpiperidine Trihydrate with Water 20 g of (4-fluorobenzyl)-(1-methylpiperidin-4-yl)amine (anhydrous) was dissolved in water (80 mL). During dissolution, the temperature was observed to rise from 20 to 28° C. The mixture was then cooled to 15° C., and during the cooling step the formation of white crystals was observed. After cooling, the mixture was allowed to stir at 15° C. for 1 hour, after which the precipitate was filtered under suction and washed with cold water (80 mL) and dried under suction. 4-(4-fluorobenzylamino)-1-methylpiperidine trihydrate was obtained 23.4 g (94%)>99% GC purity as white crystals, with a melting point of 37-42° C. (DSC) at 10° C./min.

Example 3: Preparation of 4-(4-fluorobenzylamino)-1-methylpiperidine Trihydrate with 10% Methanol in Water 10 g of (4-fluorobenzyl)-(1-methylpiperidin-4-yl)amine (anhydrous) was dissolved in mixture of water (36 mL) and methanol (4 mL). The mixture was then cooled slowly to 7° C., during which the formation of white crystals was observed. After cooling, the mixture was allowed to stir at 7° C. for 1 hour, after which the precipitate was filtered under suction and washed with cold water/methanol 9:1 (20 mL) and dried under suction. 4-(4-fluorobenzylamino)-1-methylpiperidine trihydrate was obtained 12.0 g (96%)>99% GC purity as white crystals, with a melting point of 37-42° C. (DSC) at 10° C./min.

Example 4: Preparation of 4-(4-fluorobenzylamino)-1-methylpiperidine Trihydrate with 10% THF in Water 10 g of (4-fluorobenzyl)-(1-methylpiperidin-4-yl)amine (anhydrous) was dissolved in mixture of water (36 mL) and THF (4 mL). The mixture was then cooled slowly to 5° C., and during which the formation of white crystals was observed. After cooling, the mixture was allowed to stir at 5° C. for 1 hour, after which the precipitate was filtered under suction and washed with cold water/THF 9:1 (20 mL) and dried under suction. 4-(4-fluorobenzylamino)-1-methylpiperidine trihydrate was obtained 12.0 g (96%)>99% GC purity as white crystals, with a melting point of 37-42° C. (DSC) at 10° C./min.

Example 5: Preparation of 4-(4-fluorobenzylamino)-1-methylpiperidine Trihydrate with 10% KCl Solution in Water 10 g of (4-fluorobenzyl)-(1-methylpiperidin-4-yl)amine (anhydrous) was dissolved in 10% KCl solution in water (40 mL). The mixture was then cooled slowly to 15° C., and during which the formation of white crystals was observed. After cooling, the mixture was allowed to stir at 15° C. for 1 hour, after which the precipitate was filtered under suction and washed with cold water (20 mL) and dried under suction. 4-(4-fluorobenzylamino)-1-methylpiperidine trihydrate was obtained 12.1 g (97%)>99% GC purity as white crystals, with a melting point of 37-42° C. (DSC) at 10° C./min.

Example 6: Purification of 4-(4-fluorobenzylamino)-1-methylpiperidine by Conversion to 4-(4-fluorobenzylamino)-1-methylpiperidine Trihydrate The crude 4-(4-fluorobenzylamino)-1-methylpiperidine obtained by the process described in Example 1, and 4-(4-fluorobenzylamino)-1-methylpiperidine obtained directly from commercial suppliers contained the following impurities:

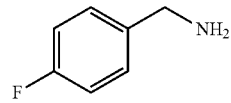

I

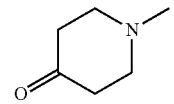

II

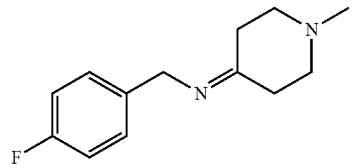

III

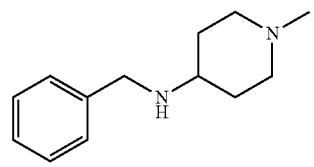

IV

Conversion of the crude 4-(4-fluorobenzylamino)-1-methylpiperidine to 4-(4-fluorobenzylamino)-1-methylpiperidine trihydrate allowed purification of the crude material to provide 4-(4-fluorobenzylamino)-1-methylpiperidine trihydrate with GC purity>99%.

TABLE 1

Impurities in two batches of commercially sourced 4-(4-fluorobenzylamino)-1-methylpiperidine (Amine) before and after conversion to 4-(4-fluorobenzylamino)-1-methylpiperidine trihydrate (Trihydrate) as identified by GC

| Batch 1 | | Batch 2 | |
| --- | --- | --- | --- |
| Amine Impurity/(% impurity) | Trihydrate Impurity/(% impurity) | Amine Impurity/(% impurity) | Trihydrate Impurity/(% impurity) |
| *RRT 0.32/(1.81) | RRT 0.32/(0.00) | II/(0.11) | II/(0.00) |
| RRT 0.96/(0.23) | RRT 0.96/(0.01) | I/(0.18) | I/(0.01) |
| RRT 1.04/(0.92) | RRT 1.04/(0.12) | III/(0.42) | III/(0.00) |
| IV/(0.05) | IV/(0.03) | RRT 1.52/(0.30) | RRT 1.52/(0.00) |
| Amine - 96.38% pure | Trihydrate - 99.32% pure | Amine - 97.91% pure | Trihydrate - 99.15% pure |

*RRT - unidentified impurities characterised by retention time.

Example 7: Stability of 4-(4-fluorobenzylamino)-1-methylpiperidine by Conversion to 4-(4-fluorobenzylamino)-1-methylpiperidine trihydrate The stability of the crude 4-(4-fluorobenzylamino)-1-methylpiperidine oil obtained by the process described in Example 1 was also assessed.

TABLE 2

Stability of 4-(4-fluorobenzylamino)-1-methylpiperidine in a sealed container at 1 and 2.5 months

| Batch 3 -impurity/(% impurity) | | Batch 4 - impurity/(% impurity) | |
|---|---|---|---|
| 0 months | 1 month | 0 months | 2.5 months |
| II/(0.12) | II/(0.21) | II/(0.12) | II/(0.14) |
| I/(0.21) | I/(0.26) | I/(0.23) | I/(0.18) |
| III/(0.27) | III/(0.59) | III/(0.68) | III/(1.15) |
| Amine - 98.17% pure | Amine - 97.66% pure | Amine - 97.82% pure | Amine - 97.09% pure |

The crude 4-(4-fluorobenzylamino)-1-methylpiperidine oil decreased in purity by 0.5% after 1 month and 0.7% after 2.5 months.

Comparatively, 4-(4-fluorobenzylamino)-1-methylpiperidine trihydrate stored under the same conditions was stable, and no decomposition was observed.

Example 8: Preparation of Pimavanserin from 4-(4-fluorobenzylamino)-1-methylpiperidine Trihydrate Boc$_2$O (30.0 g) and DMAP (2.7 g) were dissolved in DCM (115 mL) at room temperature and cooled to −18° C. A solution of 1-[4-(2-methylpropyloxy)phenyl]methanamine (20.2 g) in a mixture of DCM 600 mL and triethylamine 16 mL was added dropwise to the reaction mixture over 40-90 minutes keeping internal temperature below −5° C. 4-(4-fluorobenzylamino)-1-methylpiperidine trihydrate (42 g) taken directly from crystallization was added and the reaction mixture was heated to 0° C. and then to 35° C. and stirred at this temperature for 30 minutes. The reaction mixture was then washed twice with a solution of hydrochloric acid and NaCl in a water/methanol mixture and twice with a solution of NaCl in a water/methanol mixture. After the extractions the organic solvent was removed by atmospheric distillation and the remaining oil was dissolved in water/methanol mixture. The mixture was then heated to about 40° C. and washed twice with methyl-t-butyl ether (MTBE). After the washing step, toluene (360 mL) was added and the pH of the mixture was adjusted to 7.3 with a sodium bicarbonate solution. The phases were then separated and the aqueous phase was discarded. To the organic layer a first portion of heptane (200 mL) was added, and the resulting mixture was washed with demineralised water. To the organic phase a second portion of heptane (400 mL) was added and the mixture stirred at about 40° C. until the product started to precipitate (~3 hours), at which point the mixture was then cooled to about 0° C. The product was then isolated by filtration and washed with toluene/heptane mixture and with heptane, and dried in vacuum drier to yield 39.6 g (83%) of pimavanserin base (HPLC purity 99.89%).

Example 9: Preparation of Pimavanserin from 4-(4-fluorobenzylamino)-1-methylpiperidine Trihydrate Boc$_2$O (30.0 g) and DMAP (2.7 g) were dissolved in DCM (115 mL) at room temperature and cooled to −18° C. A solution of 1-[4-(2-methylpropyloxy)phenyl]methanamine (20.2 g) in a mixture of DCM 600 mL and triethylamine 16 mL was added dropwise to the reaction mixture over 40-90 minutes keeping internal temperature below −5° C. 4-(4-fluorobenzylamino)-1-methylpiperidine (27.5 g, containing 0.2% (KF) of water prepared by azeotropic removal of water from 42 g of wet 4-(4-fluorobenzylamino)-1-methylpiperidine trihydrate containing 33% (KF) of water [MTBE-water azeotrope]) was added and the reaction mixture was heated to 0° C. and then to 35° C. and stirred at this temperature for 30 minutes. The reaction mixture was then washed twice with a solution of hydrochloric acid and NaCl in a water/methanol mixture and twice with a solution of NaCl in a water/methanol mixture. After the extractions the organic solvent was removed by atmospheric distillation and the remaining oil was dissolved in water/methanol mixture. The mixture was then heated to about 40° C. and washed twice with methyl-t-butyl ether. After the washing step, toluene (360 mL) was added and the pH of the mixture was adjusted to 7.3 with a sodium bicarbonate solution. The phases were then separated and the aqueous phase was discarded. To the organic layer a first portion of heptane (200 mL) was added, and the resulting mixture was washed with demineralised water. To the organic phase a second portion of heptane (400 mL) was added and the mixture stirred at about 40° C. until the product started to precipitate (~3 hours), at which point the mixture was then cooled to about 0° C. The product was then isolated by filtration and washed with toluene/heptane mixture and with heptane, and dried in vacuum drier to yield 40.6 g (85%) of pimavanserin base (HPLC purity 99.80%).

Example 10: Preparation and Purification of Pimavanserin Hemitartrate

The pimavanserin base (10 g, 0.0234 mol) was dissolved in a mixture of acetone (40 mL) and MTBE (100 mL) at 35-40° C. The obtained solution was filtered and a seed of pure pimavanserin hemitartrate form C (0.05 g) was added and the solution was heated to reflux (50-55° C.). After 1 hour at reflux, a solution of (1.75 g, 0.0117 mol) L-tartaric acid in acetone (60 mL) was added dropwise. The obtained suspension was stirred at reflux for 1 hour, cooled to 20-25° C. over 4 hours and stirred at 20-25° C. for 4 hours. The product was filtered off, washed with a mixture of acetone: MTBE [9] (20 mL) and with MTBE (20 mL). After drying at 50-55° C. in a vacuum dryer 11.17 g (95%, 0.0222 mol) of pimavanserin hemitartrate form C was obtained with a HPLC purity above 99.75%.

The invention claimed is:
1. 4-(4-Fluorobenzylamino)-1-methylpiperidine trihydrate.

2. A process for the preparation of 4-(4-fluorobenzylamino)-1-methylpiperidine trihydrate comprising treating 4-(4-fluorobenzylamino)-1-methylpiperidine with water.

3. A process as claimed in claim 2, comprising:
(i) dissolving 4-(4-fluorobenzylamino)-1-methylpiperidine in water to form a solution;
(ii) cooling the solution obtained in step (i) to precipitate 4-(4-fluorobenzylamino)-1-methylpiperidine trihydrate; and
(iii) isolating the 4-(4-fluorobenzylamino)-1-methylpiperidine trihydrate from the solution.

4. A process as claimed in claim 2, comprising treating 4-(4-fluorobenzylamino)-1-methylpiperidine with, or dissolving 4-(4-fluorobenzylamino)-1-methylpiperidine in, a water/alcohol mixture or a water/organic solvent mixture or an aqueous inorganic salt solution.

5. A process as claimed in claim 3, wherein in step (ii) the solution is cooled to below 20° C.

6. A process as claimed in claim 2, wherein prior to treating 4-(4-fluorobenzylamino)-1-methylpiperidine with water or prior to dissolving 4-(4-fluorobenzylamino)-1-methylpiperidine in water to form a solution, the process further comprises the step of preparing 4-(4-fluorobenzylamino)-1-methylpiperidine by reacting together 1-methyl-4-piperidone and 4-fluorobenzylamine or 4-fluorobenzaldehyde and 1-methylpiperidin-4-amine, in the presence of a reducing agent.

7. A process as claimed in claim 3, comprising treating 4-(4-fluorobenzylamino)-1-methylpiperidine with, or dissolving 4-(4-fluorobenzylamino)-1-methylpiperidine in, a water/alcohol mixture or a water/organic solvent mixture or an aqueous inorganic salt solution.

8. A process as claimed in claim 3, wherein prior to treating 4-(4-fluorobenzylamino)-1-methylpiperidine with water or prior to dissolving 4-(4-fluorobenzylamino)-1-methylpiperidine in water to form a solution, the process further comprises the step of preparing 4-(4-fluorobenzylamino)-1-methylpiperidine by reacting together 1-methyl-4-piperidone and 4-fluorobenzylamine or 4-fluorobenzaldehyde and 1-methylpiperidin-4-amine, in the presence of a reducing agent.

\* \* \* \* \*